United States Patent
Mariotti

[19]

[11] Patent Number: 5,882,589
[45] Date of Patent: Mar. 16, 1999

[54] SEALED ENDOSCOPE DECONTAMINATION, DISINFECTION AND DRYING DEVICE

[75] Inventor: Bernard Mariotti, Marseille, France

[73] Assignee: Leon Shipper, Palm City, Fla.

[21] Appl. No.: 612,180

[22] Filed: Mar. 7, 1996

Related U.S. Application Data

[63] Continuation-in-part of Ser. No. 253,460, Jun. 3, 1994.

[51] Int. Cl.⁶ .............................. A01N 25/00; A61L 2/00; A61L 9/00; B08B 1/00
[52] U.S. Cl. ................................ 422/28; 134/14; 134/18; 134/22.1; 134/22.11; 134/22.12; 134/22.18; 134/24; 134/56 R; 134/57 R; 134/99.1; 134/99.2; 134/102.2; 134/103.1; 134/104.4; 134/166 R; 134/169 C; 134/170; 134/171; 422/33; 422/255; 422/257; 422/267; 422/278; 422/297; 422/295; 422/301
[58] Field of Search ................................ 422/28, 33, 255, 422/257, 267, 278, 297, 301, 295; 134/14, 18, 22.1, 22.11, 22.12, 22.18, 24, 56 R, 57 R, 99.1, 99.2, 102.2, 103.1, 104.4, 166 R, 169 C, 170, 171

[56] References Cited

U.S. PATENT DOCUMENTS

| | | | |
|---|---|---|---|
| 4,335,075 | 6/1982 | Kackos | 422/112 |
| 4,721,123 | 1/1988 | Cosentino et al. | 134/57 |
| 4,731,222 | 3/1988 | Kralovic et al. | 422/37 |
| 4,763,678 | 8/1988 | Ott | 422/300 |
| 4,892,706 | 1/1990 | Kralovic et al. | 422/28 |
| 5,037,623 | 8/1991 | Schneider et al. | 422/292 |
| 5,077,008 | 12/1991 | Kralovic et al. | 422/37 |
| 5,091,343 | 2/1992 | Schneider et al. | 422/297 |
| 5,217,698 | 6/1993 | Siegel et al. | 422/292 |
| 5,538,638 | 7/1996 | Hedman | 210/636 |

FOREIGN PATENT DOCUMENTS 007 22 57   11/1982   European Pat. Off. .

OTHER PUBLICATIONS

Steris Corporation, Operator Manual Steris System Processor, 1988, 1990, including pp. 4–3 to 4–20.

Automate De Nettoyage Et De Desinfection Des Endoscopes Souples (1995) (with translation).

*Primary Examiner*—Patrick D. Niland
*Attorney, Agent, or Firm*—Liddell, Sapp, Zivley, Hill & LaBoon, L.L.P.

[57] ABSTRACT

A device for cleaning, disinfecting, and/or drying an endoscope consists of a basin supported on a base. The basin forms a channel that defines a teardrop shape. The device includes a lid that sealingly engages the basin. During operation, the endoscope to be cleaned is completely immersed in cleaning solution in the basin. The basin includes injectors arranged so as to create a rotating flow of cleaning liquid and sterile rinsing water or recycled drying air within the channel. The vessel also includes injection nozzles that attach to various inlets of the endoscope to inject products at specified pressures and to continuously test the tightness of the seal.

15 Claims, 5 Drawing Sheets

SEALED ENDOSCOPE DECONTAMINATION, DISINFECTION AND DRYING DEVICE

This is a continuation-in-part application of U.S. patent application Ser. No. 08/253,460, filed Jun. 3, 1994.

TECHNICAL FIELD OF THE INVENTION

The present invention relates to the decontamination arts. More particularly, it relates to a system for decontaminating, disinfecting, and sterilizing medical equipment. Still more particularly, the present invention relates to a device for decontaminating, disinfecting and sterilizing endoscopes, such as fiberscopes, video-endoscopes or echoendoscopes of all types, and similar tubular medical equipment in a fast and effective manner.

BACKGROUND OF THE INVENTION

Disinfection denotes the absence of pathogenic life forms. Sterilization connotes the absence of all life forms. Often, sterilization is measured against the elimination of bacterial endospores, which are the living organisms most resistant to conventional sterilants. "Decontamination" is used hereinafter to mean sterilization, disinfection or both.

Endoscopes are protectively encased bundles of flexible optical fibers used to transmit images to the operator at one end from otherwise inaccessible regions into which the opposite end of the instrument is inserted, so as to obtain a view of the structures surrounding such regions. Such an arrangement makes possible the visual examination, and even photographing, of structures surrounding cavities to which there is some external access, such access typically being a relatively small opening at some distance from the region of interest.

Not only can an endoscope be inserted into the region of interest and manipulated to permit viewing in different directions, but also such instruments are typically built to include means that allow the insertion of fluids into the region of interest. Often, there are also means for the removal of tissue from portions of the surrounding organ structures. Thus, in addition to the fiber optic bundle, there is usually provided a plurality of enclosed channels or passageways more or less paralleling the direction of the fiber optic bundle. These channels are also included within the enclosure that protects the fiber optic bundle. Specifically, such channels are typically provided to carry one or more of water, air and carbon dioxide gas. A further channel is often provided to permit the extension therethrough of the instrumentation needed to conduct a biopsy of tissue in the region of interest. This latter channel may also be connected to a vacuum source as a means for obtaining fluid samples. This biopsy/suction source typically has a larger diameter than the other channels.

Because endoscopes are complex, highly instrumented medical devices, they are too costly to be disposable. Therefore, it is desirable to reuse such devices. Because they are exposed to bodily fluids and tissue, both internally and externally, it is necessary to clean these devices thoroughly before they can be reused. The turn-around time on sterilization is relatively long, often on the order of days. This long turn-around time increases the need for medical decontamination equipment and requires a relatively high inventory of the devices themselves.

Medical equipment is commonly sterilized in a steam autoclave. Autoclaves kill life forms with a combination of high temperature and pressure. Autoclaves have several drawbacks. The high temperature pressure vessel tends to be bulky and heavy. Because the medical devices are made of rubber and plastic, the elevated temperature and pressure tend to reduce their durability and therefore their useful life.

Alternatively, medical equipment may be sterilized with an ethylene oxide gas, which is less damaging to the equipment than steam. However, ethylene oxide gas requires a relatively long exposure and an even longer degassing period. Also, ethylene oxide is toxic, volatile and relatively expensive.

In general, the equipment-decontamination devices presently used are generally very large machines, often of the dishwasher type variety. They are too bulky to fit easily into an endoscopy kit. In addition, they present the following disadvantages:

they require a significant volume of solution (in the order of at least 10 liters), and are therefore relatively costly to operate;

they do not contain an integrated internal and external drying function; drying is performed in an additional module and typically lasts from 15 to 25 minutes;

there is a risk of deterioration of the medical equipment, due to the lack of permanent control of its imperviousness throughout the disinfection cycle;

rinsing is not performed with sterile water;

there is a lack of automated disinfection of filters used in the device and filters clog frequently;

there is incomplete immersion of the endoscope with mechanical washing effect; it is either immersed in a static solution or sprayed by rotating arms (dishwasher type), which does not ensure the efficient loosening and removal of organic matter;

seals used to prevent leakage of the various solutions are insufficient for the use of foaming products; this lack of seal quality allows the disinfectant, which is generally noxious, to leak into the atmosphere;

no safety controls are provided to prevent the operation of a cleaning cycle in the absence of sufficient disinfectant; and the machines are endoscope-specific and do not easily accommodate different medical devices.

The device according to this invention eliminates all of the disadvantages of the prior art. The invention provides a small, upgradable device which requires only simple and limited maintenance, uses a very small volume of solution in each full cycle and provides absolute safety, the complete removal of stains, and very fast integrated drying. In addition, because of its shorter cycle time, the device of this invention reduces the number of endoscopes needed. Further, the tightness of the seal of the device not only makes it possible to use foaming products, but also eliminates any release of disinfectant odors outside of the device itself.

SUMMARY OF THE INVENTION

The invention consists of a teardrop shaped basin, into which the endoscope may be completely immersed. It is equipped with injectors arranged so as to create a rotating flow of cleaning liquid and sterile rinsing water or recycled drying air within the basin. In addition, it contains couplings which attach onto the instrument to inject products at specified pressures and to continuously test the tightness of the seal. The vessel is closed by a lid which fits tightly onto the vessel and is sealed thereby by an inflatable seal. The operations, as well as the operating controls of the invention, are performed automatically by a programmable CPU.

The present device is capable of performing the following operations successively and automatically: checking the tightness of the door; checking the sufficiency of the level of the cleaning and disinfecting products; checking the seal of the endoscope; cleaning and disinfecting; single or multiple rinsing; and drying.

BRIEF DESCRIPTION OF THE DRAWINGS

For a detailed description of a preferred embodiment of the invention, reference will now be made to the accompanying drawings wherein.

DETAILED DESCRIPTION OF THE INVENTION

Figure 1:
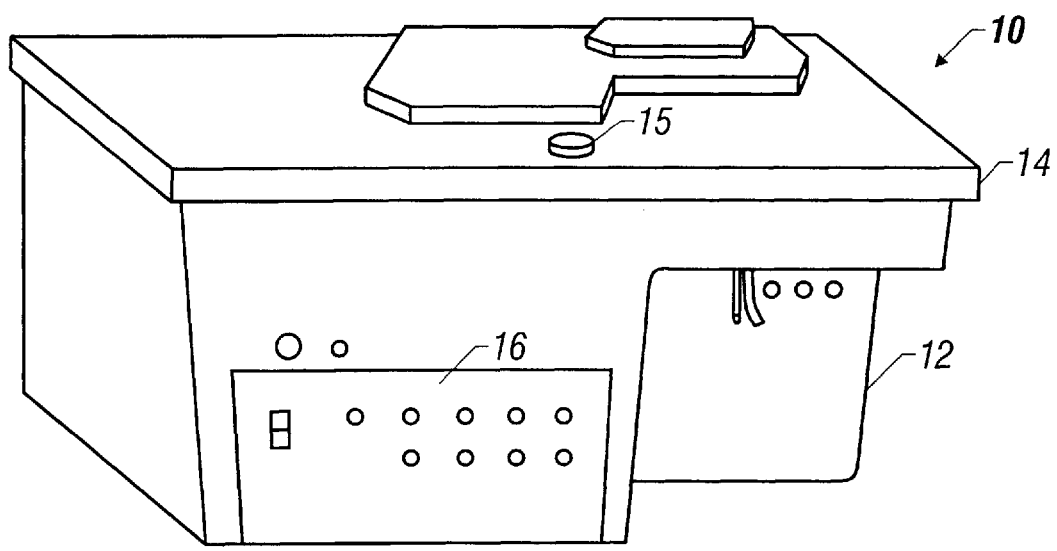
FIG. 1 is a perspective view of the present device with its lid closed.
Figure 2:
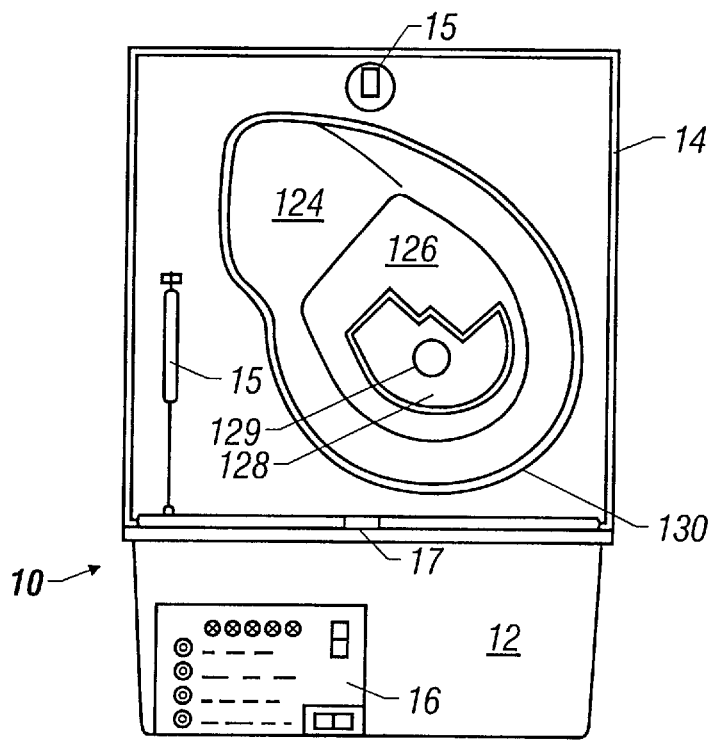
FIG. 2 is a front view of the present device with its lid raised.

Referring initially to FIGS. 1 and 2, the present equipment-washing and decontaminating device 10 comprises a base 12, a lid 14 hingedly attached to base 12, and an arm 15 for propping lid 14 open. Lid 14 includes a latch that is adapted to engage a mating latch receiving means 17 on body 12 for locking lid 14 in a closed position. Lid 14 further includes several features that enable it to engage the upper surface of base 12 in a desired manner. These features are discussed in detail below. Base 12 houses the operating elements of the device as discussed in detail below and includes on its front surface a control panel 16. Control panel 16 preferably includes a cycle selector, an on/off switch, and a number of symbols which are illuminated during the cycle stages or following various processing faults, discussed below.

Basin

Figure 3:
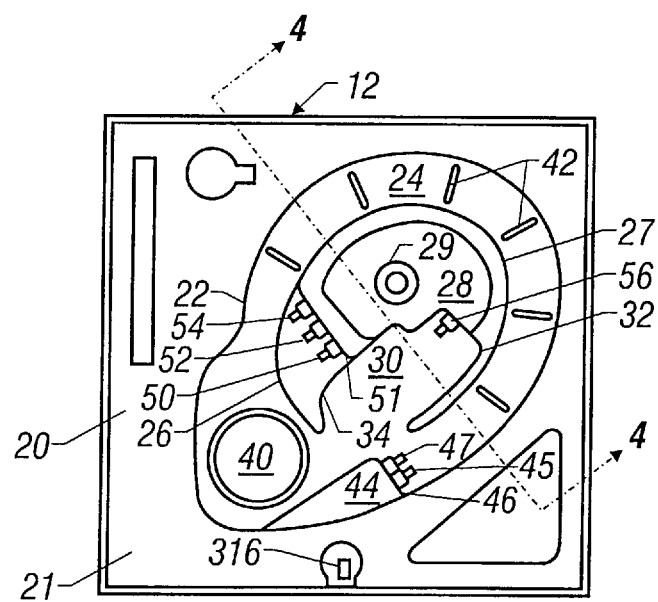
FIG. 3 is a top view of the device with the lid removed.
Figure 4:
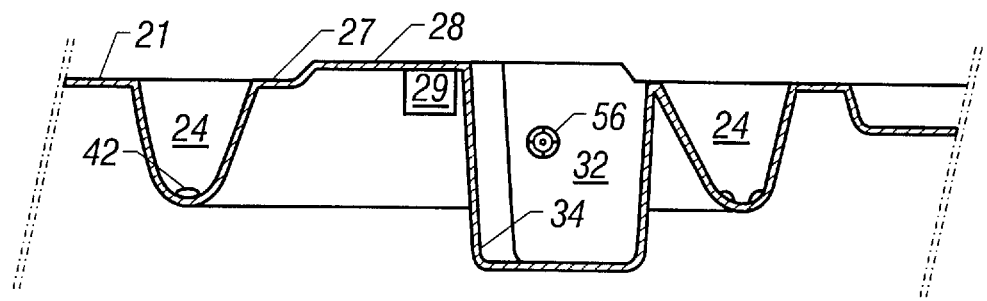
FIG. 4 is an enlarged cross section taken along line 4—4 of FIG. 2, but with the lid closed.

Referring now to FIGS. 3 and 4, base 12 includes an upper surface 20 that is contoured to define a washing basin 22. A generally planar surface 21 surrounds basin 22. The upper surface 20, including planar surface 21 and basin 22, is preferably constructed of a smooth, impervious, durable material, such as certain polymers or fiberglass. Basin 22 is generally teardrop shaped and includes a curved channel 24 encircling a raised island 26 therein. It will be understood that the shape of the channel can be varied somewhat, although it is preferred that the shape of the channel conform generally to the coiled shape of the endoscope so as to reduce the volume of fluid required to immerse the endoscope therein. Island 26 includes a top surface 27, which is at approximately the same elevation as the surrounding upper surface 21, and an upper deck 28, which is at a slightly higher elevation than upper surface 27. Upper deck 28 includes a recessed port 29 therein. Like basin 22, island 26 is generally teardrop shaped but includes a bay 30 therein. Bay 30 includes a rear wall 32 and a side wall 34.

The narrow end of basin 22 includes a drain hole 40 and is at a lower elevation than the rounded portion of channel 24 encircling island 26. The floor of channel 24 includes a plurality of molded-in supports 42, which are configured to support a endoscope or other device slightly above the floor of channel 24 and to prevent the endoscope from shifting within channel 24 once washing has begun. Basin 22 further includes a shoulder 44 near its narrow end, which includes a rearward looking face 46.

Injection System

The present device includes a plurality of inlets for supplying water, cleaning solutions and drying air to the washing chamber. Still referring to FIG. 3, shoulder 44 includes a pair of injectors 45, 47. Injectors 45, 47 are positioned so that a stream injected therefrom is substantially tangential to the perimeter of basin 22 and flows through channel 24 in a counterclockwise direction as drawn. Island 26 also includes a plurality of injectors 50, 52, 54. As shown in FIG. 3, injectors 50, 52 and 54 are mounted on a substantially vertical injector surface 51 which is part of island 26. As best shown in FIGS. 3 and 4, rear wall 32 of bay 30 also includes an air injection nozzle 56.

Lid

Referring now to FIG. 2, lid 14 is configured to substantially conform to the upper surface 20 of base 12. Thus, lid 14 includes a teardrop shaped lip 124, which encircles a depression 126. Depression 126 includes a well 128. An air exhaust 129 is located in well 128. The perimeter of lip 124 houses an inflatable sealing mechanism 130, discussed in detail below.

Figure 5:
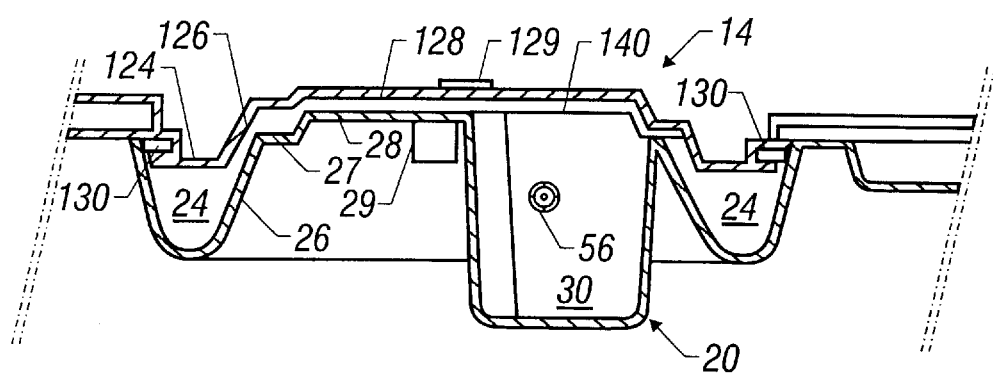
FIG. 5 is the same cross section shown in FIG. 4, but with the lid closed.

Referring now to FIG. 5, lip 124 is configured to be received in channel 24, depression 126 conforms to island 26, and well 128 conforms generally to upper deck 28. As shown in FIG. 4, lid 14 does not contact upper surface 20 except at the interface formed by engagement of inflatable seal 130 with basin 22. Within the sealed area, the corresponding surfaces of upper surface 20 and lid 14 define a narrow channel 140, which opens into basin 22 and channel 24.

Fluid System

Figure 6:
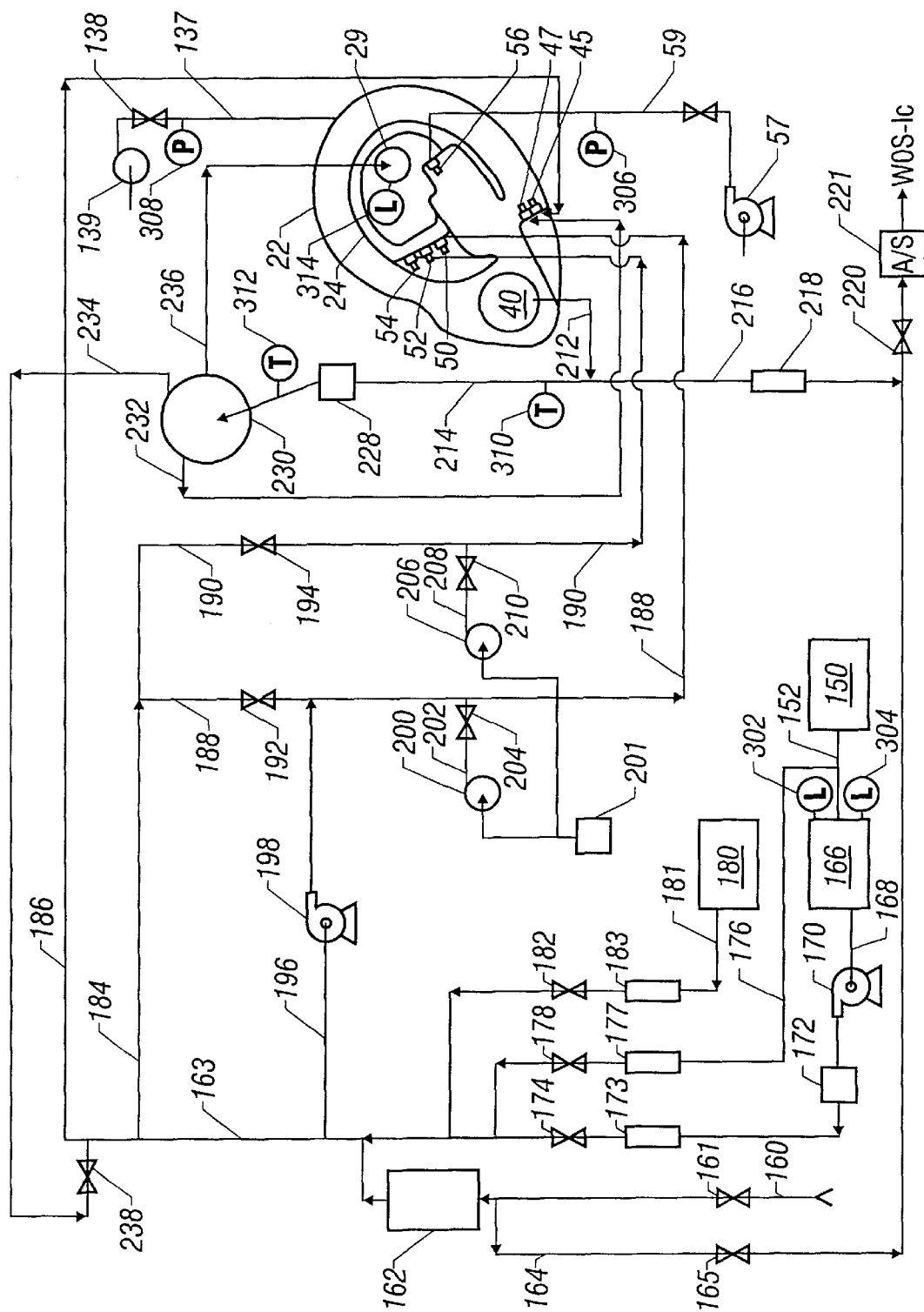
FIG. 6 is a schematic diagram of the fluid lines of the present device.

Referring now to FIG. 6, the fluid lines connecting the mechanical elements described above are as follows. Water is provided to the system through water inlet line 160 which feeds a water filter 162. According to a preferred embodiment, water is provided to water inlet line 160 from a conventional external source at a pressure of approximately 3.5 to 4 bars. Still more preferably, the inlet water is preheated to abourt 45° C. Filter 162 is preferably a 0.2 micron filter. A solenoid valve 161 controls the flow of water through line 160. Water leaving filter 162 flows through line 163. A drain line 164 is also connected to filter 162. Check valve 165 controls fluid flow through line 164.

Disinfectant is provided to the system from a disinfectant measuring tank 166 housed in base 12. Measuring tank 166 is in turn supplied with disinfectant from a storage tank or dispensing container 150 by pump 154 via line 152. Disinfectant flows from measuring tank 166 through line 168, pump 173 and check valve 174 before entering line 163. A second disinfectant flow line 176 flows through pump 177 and check valve 178 before feeding into line 163.

Detergent enters the system from detergent tank 180 housed in base 12. In order to prevent any handling of the products to be injected, both disinfectant and detergent, these products can be supplied in disposable containers, which can take the place of tanks 150 and 180. Detergent flows through line 181 into line 163. The flow of detergent through line 181 is controlled by check valve 182.

Line 163 is divided into two streams 184, 186. Stream 186 is connected directly to injection nozzle 45 in basin 22.

Stream 184 is divided into two streams 188, 190 which pass through check valves 192, 194, respectively. An additional stream 196 is fed by line 163 and pressurized by booster pump 198. Stream 196 supplements stream 188. In this manner the pressure in stream 188 is increased above that in stream 190. Stream 188 is fed with compressed air provided by compressor 200 via stream 202 and check valve 204. Stream 190 is provided with compressed air from compressor 206 via stream 208 and check valve 210. A filter 201 is preferably provided upstream of compressors 200, 206. Filter 201 is preferably a 0.22 micron filter. Stream 188 feeds injection nozzle 50. Stream 190 feeds injection nozzle 54. It will be understood that middle injection nozzle 52, and as many additional nozzles as desired (not shown), may be connected to either high pressure stream 188 or low pressure stream 190 to allow for washing additional large—or small—diameter endoscopic channels as needed.

Liquids supplied to basin 22 exit via drain hole 40 which drains into line 212. Drain line 212 feeds recycle stream 214 and waste stream 216. Waste stream 216 is pumped by pump 218 through check valve 220 and anti-siphoning device 221 to a conventional waste disposal line. Anti-siponing device 221 provides a discontinuity in waste stream 216, thereby preventing any backward flow of dirty liquid into the washing system. A vapor impermeable sleeve is preferred over the discharge point to the waste disposal line. Recycle stream 214 passes through a heater 228 and into recycle pump 230. Recycle pump 230 may be any suitable pump capable of providing the desired pressure increase and having three exit streams 232, 234, 236. Recycle pump 230 is preferably capable of pumping at least approximately 70 liters per minute. Alternatively, recycle pump 230 may be provided with a single exit stream that is subsequently divided into three streams. Stream 232 is recycled directly into basin 22 through injection nozzle 47. Stream 234 is recycled indirectly into basin 22 through check valve 238 and streams 184, 186. Stream 236 is recycled directly to basin 22 through a wash nozzle located in port 29 and discussed in detail below.

Nozzle 56 is provided with compressed air by compressor 57 via line 59. Inflatable seal 130 is provided with compressed air by compressor 139 via compressed air line 137 and valve 138.

Lid Washing

Figure 7:
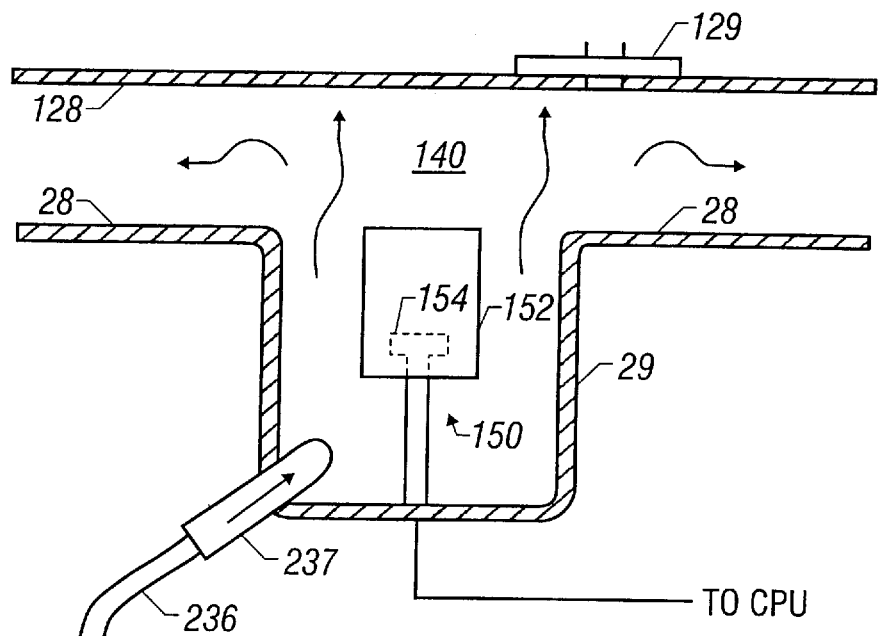
FIG. 7 is an enlarged cross section of the uppermost inlet nozzle of the present device.

Referring now to FIG. 7, stream 236 enters port 29 through was nozzle 237. Once port 29 is full, which occurs quickly as its volume is small, fluid entering through nozzle 237 flows up out of port 29 and is directed across the surfaces of upper deck 28 and well 128. From there, the fluid flows through channel 140 into basin 22.

Seal

Figure 8:
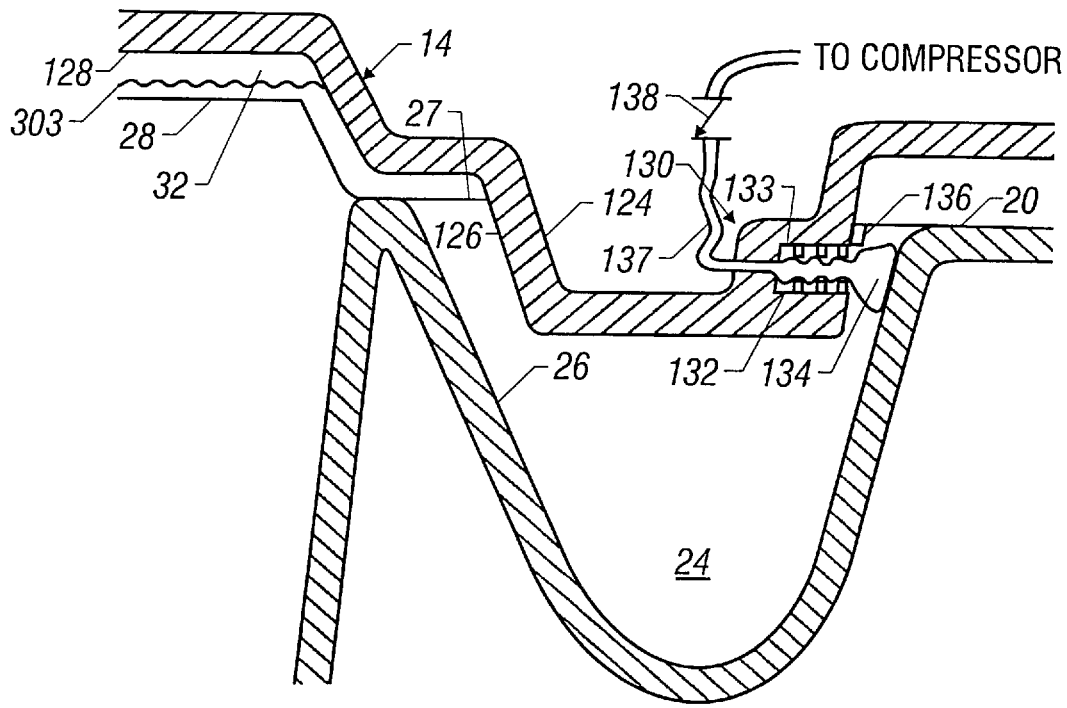
FIG. 8 is an enlargement of a portion of the cross section shown in FIG. 5.

Referring now to FIG. 8, inflatable seal 130 comprises an inflatable member 134 that is supplied with compressed air from compressor 139 (FIG. 6) via compressed air line 137. Inflatable member 134 includes a flanged collar 136 affixed thereto and is received in a peripheral groove 133 in lip 124 of lid 14. Collar 136 seals the opening of groove 133 to prevent the entry therein of cleaning fluids and/or biological contaminants. Groove 133 preferably includes a plurality of teeth or ridges 132 formed therein. Teeth 132 grip inflatable member 134 to prevent it from being dislodged from groove 133, particularly when it is inflated.

Also shown in FIG. 8 is the water level 303 that is attained during filling of the device, described below. It will be noted that level 303 is higher than the uppermost portion of upper deck 28 of island 26, and is higher than the level of seal 130 itself. Thus, at some times seal 130 functions to contain liquids within the device. As long as it is inflated, seal 130 prevents the escape of liquid, exhaust air, and vapors into the surrounding atmosphere.

Control

As stated above, base 12 includes control panel 16. Control panel 16 is electrically connected a microprocessor, or CPU, 300, which is in turn connected to the various components described above. Control panel 16 is preferably accessible from the front. CPU 300 controls the cleaning, disinfecting, rinsing and drying operations while monitoring, such operating parameters such as the level, temperature and concentration of the solutions, the tightness of the seal of the endoscope, and the operating condition of all active components throughout the disinfection cycle.

A plurality of sensors located throughout the system provide feedback to the CPU, so as to enable it to control the overall operation of the device and various components thereof. Referring to FIG. 6, the sensors include: high and low level sensors 302, 304 respectively, which monitor the level of disinfectant concentrate in tank 166; pressure sensor 306 on line 59, which monitors air pressure inside the endoscope; pressure sensor 308 on line 137, which controls the door seal pressure; water temperature sensor 310 in line 214, which monitors the temperature of the liquid leaving drain hole 40; temperature safety device 312 downstream of heater 228, which monitors the temperature of the liquid leaving heater 228; level sensor 314 in port 29, which monitors the water level in basin 22; and a latch closing sensor 316 (FIG. 3) to detect if lid 14 is open or not fully closed. Once a cycle has commenced, the lid cannot be opened until the cycle is complete. This protects the operator from exposure to the disinfectant. Level sensor 314 is preferably a float that closes an electrical contact upon reaching a predetermined liquid level (level 303).

Operation

Once the endoscope is in place in basin 22, operator input is reduced to the selection of one of the preprogrammed decontamination sequences available. The sequence is initiated by the operator at control panel 16.

Check Program

Pump 154 is activated to pump disinfectant concentrate from storage tank 150 into measuring tank 166 until the level of disinfectant concentrate in tank 166 reaches high level sensor 302. The CPU is programmed so that if high level sensor 302 is not triggered within a predetermined time after activation of pump 154 (preferably 30 seconds), the program aborts and sounds an alarm.

Provided sufficient disinfectant concentrate enters tank 166, the second check performed is an inflation of the air tight seal. Seal 130 is checked by inflating member 134 to a predetermined pressure and then monitoring its pressure for a predetermined time period, preferably 10 to 30 seconds, to confirm that there is no loss of pressure due to leakage from the seal. Pressure in member 134 is preferably monitored continuously throughout the decontamination sequence.

The third test performed by the present device is a test of the endoscope itself. This is also a leak test and is performed by pumping air through nozzle 56 to the interior channels of the endoscope. The endoscope is connected to nozzle 56 by means of quick couplings which are available to fit any type of endoscope. A storage compartment (not shown) is preferably provided within base 12 for storage of the couplings. During endoscopic operations, the interior channels of the endoscope are typically sealed to prevent the ingress of bodily fluids, as they contain the optic cables and similar sensitive equipment. During the test sequence, pressure in these channels is monitored for at least 45 seconds prior to the start of the cycle and then constantly throughout the cycle. If a pressure drop int the endoscope occurs during this period or subsequently during the various cleaning sequences, the program is aborted and an alarm sounds. Following these check programs, provided all tests are passed, the system commences the decontamination sequence.

Washing

The initial cleaning step comprises the passage of air and water through the channels of the endoscope via lines 188, 190 and nozzles 50, 54 by opening solenoid valve 161 and activating compressors 200, 206. This flushing with air and water preferably lasts for approximately 15 seconds. The purpose of this step is to flush the majority of organic debris from the inside of the endoscope. Drain pump 218 is activated during this step and recycle pump 230 is inactive, so that the flushing water is continuously withdrawn from the system, no fluids are recycled and no flushing water is present in the basin at the end of this step.

For the second cleaning step, pump 218 is deactivated and water is allowed to flow into the tank through line 163 until water in the tank reaches level 303 shown in FIG. 7. The water filling step may take approximately 30 to 120 seconds, depending on the pressure and flow of water into filter 162. As soon as level sensor 314 indicates that the water level in basin 22 has reached the desired level 303, CPU 300 activates draining pump 218 for a period sufficient to drain one-third of the water volume from basin 22. This protects seal 130 from prolonged exposure to the cleaning fluid. At the end of the partial draining period, draining pump 218 is deactivated and a desired quantity of detergent is injected by pump 183 through line 181 into line 163. At this point, a small quantity of concentrated disinfectant, preferably approximately 2 cc., is injected via line 178 into line 163. Because solenoid valve 161 is closed, the water supply through line 163 is shut off during this step and this small quantity of concentrated disinfectant remains in line 163 adjacent filter 162 and creates a chemical bacterial barrier between filter 162 and the washing fluid circuit comprising lines 184, 186, 188, 190 and 234. Once this small quantity of disinfectant is injected in line 163, the CPU activates recycle pump 230, thereby causing the detergent-containing solution to circulate through lines 232, 234 and 236. This circulation of fluid creates a powerful mechanical washing action that supplements the chemical cleaning of the detergent solution. In addition, if the temperature of the water in drain line 212 is less than 45° C., heater 228 is activated to heat the fluid to at least that temperature. At some point during this step, booster pump 198 is activated by CPU 300 for a predetermined time period, preferably approximately 30 seconds. This causes the pressure in line 188 to be increased above that in line 190, in order to compensate for the relatively smaller diameter of the endoscope's air/water channel, which is conected to nozzle 50. After a period of between approximately 2 and 6 minutes depending on the degree of washing required, drain pump 218 is activated and the hot detergent solution drains out of basin 22 and the endoscope. This draining cycle takes approximately 40 seconds.

A rinse step follows, during which drain pump 218 remains activated and solenoid valve 161 is opened to allow filtered water to flow into the machine through lines 188 and 190. This step rinses the channels of the endoscope as well as basin 22, thereby removing any loose contaminates and entrapped foam. At the end of the rinse step, drain pump 218 is deactivated.

Disinfection

During the disinfecting sequence, disinfectant concentrate is injected in two steps. The first step entails injection of approximately one half of the desired total amount of disinfectant. This first amount is injected into line 163 while solenoid valve 161 is open and water is filling the tank. Once basin 22 is full, recycle pump 230 is activated. If the temperature of the water in drain line 212 is less than 45° C., heater 228 is activated to heat the fluid to at least that temperature. Once temperature sensor 310 indicates that the temperature of the water in line 214 is at least 45° C., the second portion of disinfectant concentrate is added. If pump 173 fails to inject the balance of the disinfectant concentrate within one minute of the activation signal from CPU 300, the program aborts and an alarm is sounded. Because of the rapid fluid flow rate through recycle pump 230, the second dose of disinfectant is completely mixed into the hot water solution within a few seconds. The hot disinfectant solution is injected into basin 22 through nozzles 45, 47, 50, 54, and 237. The location and configuration of all of these nozzles is critical to the efficient and rapid decontamination achieved by the present device. As stated above, the mechanical washing action enhances the effectiveness of the cleaning solutions. Also, booster pump 198 is again activated for approximately a 30 second period to increase pressure flowing through line 188, which is connected to the air and water channel of the endoscope. The pressure in line 188 during activation of booster pump 198 is preferably at least 2 bars.

During the disinfectant solution recycle period, the CPU briefly opens solenoid valve 165. Because valve 161 is closed, pump 218 is inactive, and recycle pump 230 is creating pressure in line 163 via stream 234, hot disinfectant solution cycles backwards through filter 162 and out through stream 164 to the waste stream. This back-washing period lasts approximately 10 seconds, after which solenoid valve 165 is again closed. In this manner, filter 162 is completely disinfected during each complete washing cycle.

Also during the disinfectant solution recycle period, CPU 300 briefly activates drain pump 218 so that drain line 216 is filled with hot disinfecting solution at least as far as anti-siphoning device 221. In this manner, drain line 216 is disinfected. Following these steps, recycle pump 230 remains activated for a period of time sufficient to ensure complete disinfection of the endoscope. It is preferred that recycle pump 230 be activated in a pulsed fashion such as, for example, 15 seconds on followed by 3 seconds off.

It is preferred that the quantity of disinfectant concentrate injected during the disinfectant sequence be precisely measured so as to reduce cost and avoid toxic overusage, while ensuring that the disinfectant solution is sufficiently strong to disinfect the medical equipment. For this reason, disinfectant concentrate is added to the system batchwise, with the amount of concentrate for each complete decontamination cycle being precisely measured in tank 166. High level sensor 302 is used to limit filling disinfectant tank 166. Subsequently, a signal from low level sensor causes CPU 300 to deactivate pump 170 when the level of disinfectant in tank 166 reaches low level sensor 304. In this manner, the amount of detergent injected is always equal to the exact volumetric difference between the high and low sensor levels. According to the present invention, this volumetric difference equal approximately 65 cc. The preferred disinfectant concentrate comprises a 23% glutaraldehyde solution. According to a preferred embodiment, using 65 cc. of concentrate results in a disinfectant solution in basin 22 having a concentration of 0.125%. The precise amount of detergent injected is less critical and is controlled by using CPU 300 to activate pump 183 for a certain, predetermined length of time.

The length of the disinfectant solution recycle period varies depending on the decontamination program initially selected by the operator and may vary from approximately 2 to approximately 10 minutes. At the end of the predetermined period, CPU 300 deactivates recycle pump 230 and activates drain pump 218 so that all liquids drain from basin 22 and from the endoscope.

Rinsing

After allowing sufficient time for basin 22 to completely drain, approximately 30 sec. to one minute, CPU 300 activates solenoid valve 161 while drain pump 128 is running, so that the endoscope and basin 22 are flushed with filtered water. Flushing continues for approximately 10 to 60 sec.

Lastly, drain pump 218 is deactivated and basin 22 is allowed to fill with water up to level 303. Once water reaches level 303, solenoid valve 161 is closed, drain pump 218 is activated and all water is drained from the device.

Drying and Completion of Cycle

During the drying cycle, pumps 200 and 206 inject filtered air through nozzles 50 and 54. The endoscope test pressure is released and seal 130 is deflated. CPU 300 preferably indicates that the drying cycle is complete after 45 seconds, but continues the flow of filtered air through nozzles 50 and 54 for an additional one to four minutes if door 14 is not opened. The preferred drying time is generally in the order of three minutes, which is significantly less than the fifteen to twenty-five minutes required for the machines of the art.

The total cycle time for the preferred decontamination sequence is approximately 15 minutes if water is supplied at 45° C., ranging to about 20 minutes if the water is supplied at room temperature.

By virtue of the foregoing, the present device is able to decontaminate an endoscope quickly and effectively without requiring any operator input or effort once the program is initiated. While a preferred embodiment of the invention has been shown and described, modifications thereof can be made by one skilled in the art without departing from the spirit of the invention.

For example, other programs that may be included in the CPU as desired are:

Cycle described above plus an extra rinse,

Cycle described above with a 10 minute disinfectant contact time,

Cycle described above but without cleaning (ie, first cycle of the day),

Cycle described above but 10 minute drying cycle only,

Machine self-disinfect cycle, including backwashing the integral 0.2 micron water filter and drain tubing, Drain cycle only Other Advantageous Features of the Present System Channel 24 is designed to comply with the morphology of the instruments received therein, so as not to cause deformation of the insertion tubes or light guides. Injectors 45 and 47 are arranged in basin 22 so as to cause a fluid flow that is focused on the outside of the endoscope. The endoscope is maintained in the center of said conduit by supports 42, to ensure a proper distribution of the rotating flow and to prevent liquid retention areas that could extend the drying time.

In order to prevent any confusion during the connections, the following injectors and fittings are preferably identified by markings on upper surface 20: air/water channel (inlet 50), biopsy/suction channel (inlet 54), vacuum conduit, water injection (inlets 45, 47), and tightness test (inlet 56).

Drying air pulsated through and around the endoscope enters a closed circuit, which provides for the recovery of air downstream from the protective filter. This circuit is closed during all phases of the cycle, excluding the drying. This arrangement prevents the release of air into the room and extends the life of the filter.

The present device uses only sterile water. The water filter is automatically decontaminated, disinfected and rinsed by the machine, in order to slow down clogging and provide safety.

The present device preferably includes a cycle counter (not shown) to facilitate maintenance.

It is essential that the disinfection process be completely isolated and protected from any risk of external contamination. According to the present invention, this result is achieved by the combination of inflatable seal 130; disinfection of the draining circuit; filtration of the rinsing water intake; filtration of pulsated air during the drying phase; complete absence of areas within the basin not in contact with the disinfectant; reinitialization of the program if the door is opened during the cycle, or in the event of a power outage; and use of a rinsing product that is not subject to contamination.

Only a few minutes of monitoring is required during the initial phase of the test, as it interrupts automatically the program (with visual and sound alarm) in the following cases:

insufficient quantity of disinfectant available to start the selected program;

endoscope not tight; and insufficient seal of the inflatable joint 130.

Furthermore, at the end of the program, the CPU displays a validation signal on control panel 16. If this signal is absent, the user may not consider the endoscope to be properly disinfected, and should repeat the program after determining the cause of the interruption.

In the event of an accidental outage of power, CPU 300 will reinitialize automatically the program, without requiring any intervention.

In order to provide for the implementation of strict protocols and to guarantee the reproductivity of the results, it is necessary to be able to continuously control the main parameters affecting the efficacy of the decontamination process. Hence, the present device is operated by a programmable CPU 300 and any anomaly that is liable to affect the decontamination process will automatically abort the program.

In order to optimize decontamination, the present device implements a triple operation:

1. Chemical Action. The endoscope is initially cleaned in a hot detergent and decontaminating solution to ensure the practically total elimination of organic matter. Any potential support of germs is thereby removed through the solution of proteins and saponification of fatty matter. After rinsing, the endoscope is disinfected in a hot disinfecting solution, such as for example, a glutaraldehyde-based solution, which is dispensed in a measured amount by the CPU during each cycle. This solution provides bactericidal, virucidal, algaecidal, fungicidal and sporicidal activity.

2. Mechanical action. As the endoscope is fully enclosed and immersed in a powerful rotating flow, while the internal circuits are irrigated separately at specified pressures. The pressure within an irrigated channel is preferably 0.5 bar to 0.8 bar, depending on the type of channel. The solutions are injected in all areas of the instrument, and the risks of sedimentation, clogging or obstruction of these circuits are eliminated by the forced turbulent flow.

3. Thermal Action. The chemical and mechanical actions are optimized by the maintenance of the solutions at a temperature ranging from 25° to 60° C.

Over 50% of the repair budget of soft endoscopy equipment is directly or indirectly linked to the loss of tightness with ensuing penetration of liquid. The device of this invention significantly prevents such damages. First, it authorizes the starting of the program only if the endoscope is leak-free. Secondly, and in order to detect either microleaks or sudden leaks resulting from the unplugging of channels, the automaton monitors the seal of the endoscope throughout the cycle. A leak, even if it is minor, causes the program to stop immediately. Drainage of vessel 2 is then completed and air is blown into the endoscope to maintain excess pressure therein. This prevents the penetration of water, as well as a visual and sound alarm.

Due to its small size, quiet operation and absence of smell, the present device is compatible with the configuration of any room, and readily fits on a bench top, thus eliminating costly arrangement work. It may also be installed in an endoscopy room. Its characteristics comply with specifications that are the result of the observation of several hundred endoscopy services, as well as the technical follow-up of more than a thousand endoscopes.

The positioning of the different components gives the present device a maximum of useful effects that cannot be obtained by the devices of the prior art.

MICROBIOLOGICAL TESTS

The effectiveness of the machine was tested using an artificially contaminated gastroscope. Overnight broth cultures of two test organisms were used, namely *Pseudoniollas aeruginosa* NCTC 6749 (UK disinfectant test strain—chemically tolerant vegetative bacteria) and *Enterococcus faecalis* NCTC 775 (UK disinfectant test strain—heat/chemically tolerant vegetative bacteria). Twenty cycles were performed using each of the two test organisms. The cultures were supplemented with 10% horse serum as an organic load and 20 ml flushed through all four channels (biopsy, suction, air and water) of an Olympus GIF Q10 submersible gastroscope using an all-channel irrigation device (Olympus CW3). Excess fluid was expressed using an air filled syringe. The gastroscope was left at room temperature for 10 minutes to dry before sampling (for control/pre-disinfection count) or processing and sampling (post-disinfection count). External surfaces were painted with the test soil/microorganisms. The horse serum was added to the broth to simulate the organic load likely to be encountered when an endoscope is used. All channels of the test endoscope were sampled individually, before and after disinfection, to establish the pre-and post-processing counts. The difference between the counts was used to determine the effectiveness of the decontamination (ie. cleaning and disinfection) procedure. Channel washings were suitably diluted and plated onto blood agar using a surface dropping technique. Culture plates were incubated for 18 hours at 37° C. and surviving test organisms enumerated. The results of automated cleaning and disinfection were expressed as $Log_{10}$ reductions calculated according to the following equation:

$$Log_{10}\text{ pre-disinfection} - Log_{10}\text{ post disinfection} = Log_{10}\text{ reduction}$$

The greater the $Log_{10}$ reduction, the more effective the cleaning and disinfection procedure: The four channels of the test instrument were sampled as follows:

Biopsy channel

A short piece of tubing was attached to a 10 ml syringe and the biopsy port. Ten ml of sterile water was flushed down the biopsy channel and the sample collected in a sterile bottle at the distal tip.

Suction channel

Tubing and a 10 ml syringe were attached to the suction port on the light guide connector and water flushed along the entire length of the suction channel. To do this the biopsy/suction feed button was depressed while the water was introduced and the sample was collected in a sterile bottle at the distal tip.

Air channel

The air channel was irrigated with 10 ml of sterile water from the inlet port on the light guide connector and water slowly flushed along the air channel. To do this, the water port on the light guide connector was covered with a finger and the air/water trumpet valve on the control box covered but not depressed while the sterile water was flushed along the channel. The sample was collected at the distal tip in a sterile bottle.

Water channel

Tubing and a 10 ml syringe were attached to the water inlet on the light guide connector and 10 ml of sterile water was flushed along the channel. To do this, the air/water trumpet valve on the control box was depressed and the sample collected at the distal tip in a sterile bottle.

The outside of the endoscope, eg. insertion tube, distal tip, light guide connector, valve housings etc was sampled using swabs and the samples plated onto blood agar, incubated at 37° C. for 18 hours and surviving test organisms recorded.

Results

Following initial tests, $Log_{10}$ reductions obtained from each of the four channels were unsatisfactory, i.e. in some tests, reductions of less than 5 $Log_{10}$ were obtained. An endoscope washer/disinfector that achieves a mean $Log_{10}$ reduction of 6 with no individual reductions less than 5 $Log_{10}$ after challenging with a vegetative bacteria (ie. *Pseudomonas aeruginosa* or *Enterococcus faecalis*) is considered acceptable.

Several possible explanations for the poor performance of the machine in the foregoing tests were investigated. As a result of the investigation, a new machine was installed with an integral bacteria retaining filter 602 and two additional preliminary external water filters (one particulate, one bacteria retaining). A mixer valve was also introduced to increase the temperature of the supply.

Additional tests were then carried out to establish the machine's performance and the results are expressed in Table 5.

TABLE 5

| | Mean $Log_{10}$ Reductions After 20 Cycles (Range per ml.) | | | |
| --- | --- | --- | --- | --- |
| Organism | Biopsy Channel | Suction Channel | Air Channel | Water Channel |
| *Pseudomonas aeruginosa* NCTC 6749 | 7.75 (6.86–8.34) | 6.80 (5.12–8.04) | 7.91 (6.67–8.36) | 7.84 (6.33–8.26) |
| *Enterococcus faecalis* NCTC 775 | 6.96 (5.01–8.18) | 7.32 (5.16–8.15) | 7.55 (6.14–7.95) | 7.59 (6.42–8.15) |

The mean $Log_{10}$ reductions in channel washings are shown in table 5. On all occasions the mean $Log_{10}$ reductions of *Pseudomonas aeruginosa* and *Enterococcus faecalis* were greater than 6 $Log_{10}$ with no individual reduction of less than 5 $Log_{10}$. This meets the test criteria for an endoscope washer/disinfector.

Organisms painted onto the external surfaces of the endoscope were removed or destroyed during the cycle and were not therefore recoverable using a swabbing-technique.

Glutaraldehyde Assays

An assessment was made of the concentration of glutaraldehyde in the endoscope/processing tray during the disinfection process. This was done by collecting samples of the discarded disinfectant from the drain on completion of the disinfection stage of the cycle. Also sampled was the concentration of glutaraldehyde in the rinse water. This was sampled at the discharge point to the drain. In this machine, the rinse water is not re-used. Assays were performed by the Quality Control Laboratory, Pharmacy Department, City Hospital NHS Trust. The technique used to assay the glutaraldehyde concentrations was as follows:

Disinfectant: Potentiometric Method (Johnson & Johnson)

Five mls of sample were placed into a 100 ml beaker and approximately 50 ml of deionized water added. The pH of the solution was measured while continuously stirring. The initial pH of the glutaraldehyde solution was adjusted to 3.0 with 10% (w/v) hydrochloric acid. Fifteen mls of pH adjusted 10% (w/v) hydroxylamine hydrochloride was added and the pH dropped immediately to below pH 3.0. After 5 mins, or until the pH had stabilized, the solution was titrated to pH 3.0 with 0.1 M sodium hydroxide. The volume used was recorded in mls. NaOH was factorized against the 0.1 M HCl at least monthly.

The calculation was performed as follows:

$$\% \text{ glutaraldehyde} = \frac{v \times M \times 50 \times -100 \times F}{100 \times 5}$$

where:

v=volume in mls of NAOH used.

M=molarity of NAOH

F=factor for NAOH

50=equivalent weight of glutaraldehyde

100=percent conversion

5=volume in mls of sample

A further assay was conducted using the colorimetric method but in this instance, disinfectant samples were diluted 1:100 before analysis.

Colorimetric method

The method used to detect traces of glutaraldehyde in the rinse water was as follows: Duplicate samples (5 ml) were transferred to 50 ml volumetric flasks, diluted to volume with an aqueous solution of 0.05% w/v 3=methyl-2-benzothiazolinone hydrazone hydrochloride and allowed to stand at room temperature for 20 mins. Aliquots of 15 ml were transferred from each flask to separate stoppered flasks. To these were added an aqueous solution (2 ml) of 1.6% w/v sulfuric acid plus 1% w/v ferric chloride hexahydrate. The flasks were incubated at 37° C. in a water bath for 20 minutes, cooled to room temperature and the absorbance of the resulting blue-green solution measured in 1 cm path length cells at 628 nm against a water blank.

A standard solution of approximately 20 ppm glutaraldehyde was prepared by dilution of a nominally 2% solution of an accurately determined strength. Duplicate 5 ml aliquots were treated as for the samples.

A blank was prepared by treating an aliquot of 5 ml water as for the samples.

The resulting colored solutions, including the blank, were susceptible to the formation of small bubbles on the surface of the cell, causing drifting results. Thus water was used in the reference cell to avoid this problem. All results are corrected for the absence due to the blank and are obtained immediately after the sample cell is placed in the spectrophotometer.

Results

Disinfectant mean 0.135% w/v (range 0.133–0.136% w/v) rinse water mean 18 ppm (range 17–20 ppm)

The equipment dilutes the glutaraldehyde satisfactorily. Measured levels were 8% higher than the predicted concentration of 0.125%. The glutaraldehyde concentration in the rinse water is lower than that seen with other types of endoscope washer/disinfector utilizing 2% glutaraldehyde, but as the rinse water is not reused this is of little relevance.

Microbiological Tests: Machine Self-Disinfection

A self-disinfect cycle is programmed into the machine (program 6). This cycle takes approx. 30 mins and is recommended to be used at the end of each day or on completion of the list. 4×1.8 g Sodium dichloroisocyanurate tablets, i.e. to yield a concentration containing 1000 ppm available $Cl_2$ should be used for disinfection.

The tablets used for machine disinfection were supplied by Sanichlor-G H Wood, David Murray John Building, Swindon, Wiltshire SN1 1NH. Four of these were placed in the base of the tray of the endoscope washer/disinfector before closing the lid and activating cycle 6. When dissolved, these give a concentration of 1000 ppm av $C_{12}$. The efficacy of the self disinfect cycle was assessed by contaminating the machine by pouring 50 mls of an over night suspension of *Pseudomonas aeruginosa* (108 organisms/ml) containing 10% horse serum, over the edges and interior of the tray and allowing this to dry/disperse for 30 mins before running a self-disinfect' cycle. Three such cycles were investigated and, at the end of each of these, a sterile swab was used to sample tray surfaces and other recesses where contamination may have remained.

Results

No surviving test organisms were recovered from the tray or recesses after the "self-disinfect" cycle had been run. However, it is advisable to repeat the machine self disinfect procedure immediately prior to each session as residual or environmentally associated micro-organisms may proliferate within the machine between sessions. Micro-organisms may also be introduced with the rinse water and regular disinfection of external filters and pipework may also be necessary.

What is claimed is:

1. A device for decontaminating an endoscope, said device comprising:

a substantially teardrop shaped basin having an island therein, said basin comprising walls and a floor and having a narrow end and a rounded end, said island including at least two interior-washing fluid injection nozzles oriented toward said narrow end of said basin, said basin further including a shoulder supporting at least one exterior-washing injection nozzle oriented substantially tangentially toward said rounded end of the basin;

said floor of said basin being at its lowest point at said narrow end, at its highest point at said rounded end, and having an incline therebetween;

a fluid supplying means comprising a single fluid stream that is divided between said interior-washing and exterior-washing injection nozzles, such that the interior and exterior of the endoscope can be washed simultaneously with identical fluid streams, said single fluid stream including a water feed line having a filter therein;

an injection means for introducing a quantity of concentrated disinfectant immediately downstream of said water filter so as to form an antimicrobial barrier at that point; and a lid having a seal adapted to sealingly engage the perimeter wall of said basin.

2. The device according to claim 1 wherein said island includes an upper deck and said lid includes a well, such that when said lid is sealed in said basin and said basin is filled with a liquid to the level of said upper deck, that portion of said lid within said seal with the exception of said well is immersed in said liquid.

3. The device according to claim 1 wherein said disinfectant injection means is between said water filter and said single fluid stream.

4. The device according to claim 1, further including a flow control valve upstream of said filter and a drain line connected to the upstream end of said filter such that when said flow control valve is closed, said filter can be backwashed into said drain line without removing said filter from said device.

5. The device according to claim 1 wherein a first one of said interior-washing nozzles is adapted to be connected to the biopsy/suction channel of the endoscope and is provided with fluid at a first pressure, and a second one of said interior washing nozzles is adapted to be connected to the air/water/erector channel of the endoscope and is provided with fluid at a second pressure, said second pressure being greater than said first pressure.

6. The device according to claim 1 further including a basin drain line and means for disinfecting said basin drain line during each complete washing sequence.

7. A device for decontaminating an endoscope, said device comprising:

a single substantially teardrop basin for cleaning, disinfecting and/or sterilizing and drying the device, said basin having an island therein, said basin comprising walls and a floor and having a narrow end and a rounded end, said island including at least two interior-washing fluid injection nozzles oriented toward said narrow end of said basin, said basin further including a shoulder supporting at least one exterior-washing injection nozzle oriented substantially tangentially toward said rounded end of the basin;

said floor of said basin being at its lowest point at said narrow end, at its highest point at said rounded end, and having an incline therebetween;

means for supplying a desired fluid to said interior-washing and exterior-washing injection nozzles;

a lid having an inflatable seal adapted to sealingly engage the perimeter wall of said basin, the seal housed in a peripheral groove in said lid, and having a flanged collar affixed thereto which spans the opening of said groove when said inflatable seal is received therein.

8. The device according to claim 6 wherein said island includes an upper deck and said lid includes a well, such that when said lid is sealed in said basin and said basin is filled with a liquid to the level of said upper deck, that portion of said lid within said seal with the exception of said well is immersed in said liquid.

9. A device according to claim 6 wherein said means for supplying a desired fluid comprises a single fluid stream that is divided between said interior-washing and exterior-washing injection nozzles, such that the interior and exterior of the endoscope can be washed simultaneously with identical fluid streams.

10. The device according to claim 9 wherein said single fluid stream includes a water feed line having a two micron filter therein.

11. The device according to claim 10 further including means for injection of a quantity of concentrated disinfectant immediately downstream of said water filter so as to form an antimicrobial barrier at that point.

12. The device according to claim 11 wherein said disinfectant injection means is between said water filter and said single fluid stream.

13. The device according to claim 10, further including a flow control valve upstream of said filter and a drain line connected to the upstream end of said filter such that when said flow control valve is closed, said filter can be backwashed into said drain line without removing said filter from said device.

14. The device according to claim 6 wherein a first one of said interior-washing nozzles is adapted to be connected to the biopsy/suction channel of the endoscope and is provided with fluid at a first pressure, and a second one of said interior washing nozzles is adapted to be connected to the air/water/erector channel of the endoscope and is provided with fluid at a second pressure, said second pressure being greater than said first pressure.

15. The device according to claim 6 further including a basin drain line and means for disinfecting said basin drain line during each complete washing sequence.

* * * * *

UNITED STATES PATENT AND TRADEMARK OFFICE
CERTIFICATE OF CORRECTION

PATENT NO.   : 5,882,589
DATED        : March 16, 1999
INVENTOR(S)  : Bernard Mariotti It is certified that error appears in the above-identified patent and that said Letters Patent is hereby corrected as shown below:

Column 15, Claim 7, line 31, after "teardrop" add -- shaped --.

Column 16, Claim 8, line 7, change "6" to -- 7 --.

Column 16, Claim 9, line 13, change "6" to -- 7 --.

Column 16, Claim 14, line 34, change "6" to -- 7 --.

Column 16, after Claim 15, add the following claim:

-- 16. The device according to Claim 7, wherein said basin has a volumetric capacity of less than or equal to five liters. --

Signed and Sealed this

Eighteenth Day of July, 2000

Attest:

Q. TODD DICKINSON

Attesting Officer

Director of Patents and Trademarks